United States Patent [19]

Ohmori et al.

[11] Patent Number: 4,638,041
[45] Date of Patent: Jan. 20, 1987

[54] FLUOROOXYALKYL VINYL ETHERS

[75] Inventors: Akira Ohmori; Nobuyuki Tomihashi; Hiroshi Inukai; Kazuhiro Nakai, all of Osaka, Japan

[73] Assignee: Daikin Industries, Ltd., Osaka, Japan

[21] Appl. No.: 784,590

[22] Filed: Oct. 4, 1985

Related U.S. Application Data

[62] Division of Ser. No. 713,609, Mar. 19, 1985, Pat. No. 4,568,773.

[30] Foreign Application Priority Data

Mar. 22, 1984 [JP] Japan ................................. 59-55724

[51] Int. Cl.$^4$ ............................................. C08F 14/18
[52] U.S. Cl. .................................................... 526/247
[58] Field of Search ........................................ 526/247

[56] References Cited

U.S. PATENT DOCUMENTS 3,394,116 7/1968 Sorkin .................................. 526/247
3,773,728 11/1973 Wasley et al. ...................... 526/247

Primary Examiner—Harry Wong, Jr.
Attorney, Agent, or Firm—Birch, Stewart, Kolasch & Birch

[57] ABSTRACT

A polymer comprising fluorooxyalkyl vinyl ether of the formula:

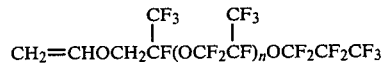

wherein n is an integer of 0 to 5.

4 Claims, No Drawings 4,638,041

FLUOROOXYALKYL VINYL ETHERS

This application is a divisional application of Ser. No. 713,609, filed on Mar. 19, 1985, and now issued into mature U.S. Pat. No. 4,568,773.

FIELD OF THE INVENTION

The present invention relates to fluorooxyalkyl vinyl ethers and homo- or co-polymers thereof.

BACKGROUND OF THE INVENTION

Perfluorooxyalkyl vinyl ether of the formula:

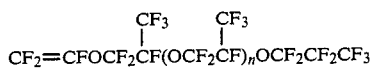
(1)

and fluorooxyalkyl vinyl ether of the formula:

(2)

wherein n is an integre of 0 to 5 are known (cf. Japanese Patent Kokai Publication (unexamined) No. 83011/1983). Since the former ether (1) is hardly homopolymerizable, and the latter ether (2) is hardly copolymerizable with fluoroolefins such as tetrafluoroethylene and chlorotrifluoroethylene, they find only very restricted use.

SUMMARY OF THE INVENTION

Accordingly one object of the present invention is to provide fluorooxyalkyl vinyl ethers which are homopolymerizable.

Another object of the present invention is to provide fluorooxyalkyl vinyl ethers which are copolymerizable with fluoroolefins.

A further object of the present invention is to provide homo- or co-polymers of novel fluorooxyalkyl vinyl ethers.

According to the present invention, there is provided a fluorooxyalkyl vinyl ether of the formula:

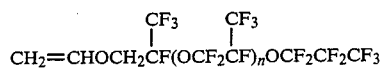
(I)

wherein n is an integer of 0 to 5.

The ether (I) of the invention may be prepared by reacting a fluorine-containing alcohol of the formula:

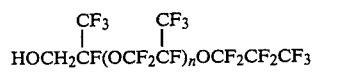
(II)

wherein n is the same as defined above with vinyl acetate in the presence of a mercury salt catalyst (e.g. mercury (II) acetate, etc.) according to a known ester-ether exchange reaction (cf. U.S. Pat. No. 739,731). This reaction is preferably carried out at a temperature of 31 20° to +10° C. Preferably, the reation is carried out in the presence of a catalyst. Specific examples of the catalyst are mercury (II) sulfate, mercury (II) acetate and sulfuric acid. Usually, the reaction is carried out in the absense of a solvent, since vinyl acetate is used in an excess amount and acts as a reaction medium. The alcohol (II) is a known compound and disclosed in, for example, Japanese Patent Kokai Publication No. 90524/1983.

In the above reaction, since the reaction product has a high percentage by weight of vinyl acetate, it is saponified with an alkaline compound such as potassium hydroxide at a temperature of 50° to 100° C., and then the ether (I) of the invention can be separated from the saponified acetate by distillation. In the saponification, little ether (I) is decomposed or polymerized.

The fluorooxyalkyl vinyl ether (I) is homopolymerizable or copolymerizable with a fluoroolefin of the formula:

wherein $X^1$, $X^2$, $X^3$ and $X^4$ are, the same or different, hydrogen, fluorine, chlorine or trifluoromethyl provided that at least one of them is fluorine or trifluoromethyl. Preferred fluoroolefins are tetrafluoroethylene, chlorotrifluoroethylene, trifluoroethylene, etc. In addition to fluoroolefins, other ethylenically unsaturated monomers (e.g. ethylene, maleic anhydride, etc.) may be copolymerized. The amount of the comonomer is preferably from 40 to 60% by mole.

Homopolymerization of the fluorooxyalkyl vinyl ether (I) of the invention may be cationically carried out in the presence of a solvent at a temperature of 31 200° to +30° C., preferably −80° to 0° C. Any cationic initiator that is used in the conventional cationic polymerization may be used, and specific examples thereof are Lewis acids such as $AlCl_3$, $SnCl_4$, $FeCl_3$, $BF_3$ and its complex with ether. The solvent may be alkones (e.g. propane, hexane, etc.), halogenated alkanes (e.g. chloromethylene, chloroethylene, carbon tetrachloride, etc.) and cyclic compounds (e.g. nitrobenzene, cyclohexane, etc.), which are liquid at the polymerization temperature.

Copolymerization of the fluorooxyalkyl vinyl ether (I) and a fluoroolefin is a radical polymerizaiton and carried in any polymerization mode such as solvent, suspension, emulsion and bulk polymerizaiton, preferably solvent polymerization. A solvent to be used in the solvent polymerization may be the same as that used in the above cationic homopolymerization. The radical initiator may be any conventionally used organic peroxide compounds and azo compounds. The polymerization temperature is preferably from 0° to 150° C.

The homo- or co-polymer of the ether (I) may be used as an elastomeric material with good low temperature characteristics, a tackifier, a water- and oil-repellent, an ink-repellent, an optical material, a gas-separating membrane, etc.

The present invention will be hereinafter explained further in detail by following Examples.

EXAMPLE 1

Preparation of

To a 1,000 ml four-necked flask,

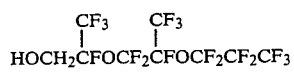

(330 g), vinyl acetate (300 g) and mercury (II) acetate (1.5 g) were added and cooled at 0° C. with a freezing mixture of ice water and sodium chloride with stirring. Then, the reaction was initiated by adding concentrated sulfuric acid (0.1 ml). The reaction was continued at a temperature of 0° to 2° C. for 9 hours. Thereafter, the reaction was terminated by adding potassium acetate (5 g).

The resultant reaction mixture was simply distilled under atmosphere pressure. A fraction distilled at a temperature not higher than 74° C. was discarded. Thereafter, the mixture was distilled under pressure of 20 mmHg and a fraction distilled in a temperature range of 35° to 90° C. was collected (190 g). To the product containing vinyl acetate, potassium hydroxide (30 g) was added and kept at 80° C. for 2 hours with stirring to saponify vinyl acetate. Then, the mixture was distilled under reduced pressure of 38 mmHg to obtain the title compound (134 g) in a temperature range of 65° to 75° C. Purity of the compound was 99.2% by weight according to gas chromatography.

IR spectrum: 1,620–1,660 cm$^{-1}$ (vinyl group).

$^1$H-NMR (No solvent. Internal standard: TMS): δ(ppm)=6.54

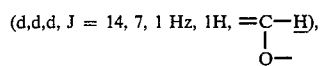
(d,d,d, J = 14, 7, 1 Hz, 1H, =C—H̲),
                                 |
                                 O—

4.46 (d, J=10 Hz, 2H, —OCH̲$_2$CF—), 4.42

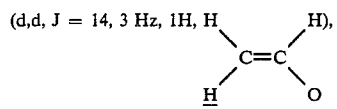
(d,d, J = 14, 3 Hz, 1H, H    H),
                        \\   /
                         C=C
                        /   \\
                       H̲     O and 4.18

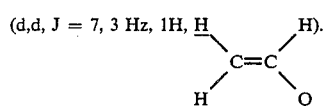
(d,d, J = 7, 3 Hz, 1H, H̲    H).
                       \\   /
                        C=C
                       /   \\
                      H     O $^{19}$F-NMR (No solvent. External standard: trifluoroacetic acid): δ(ppm)=67.9 (1F, —CF(CF$_3$)OCF$_2$CF$_2$CF$_3$), 56.8 (1F,=(C—OCH$_2$CF(CF$_3$)—), 53.0 (2F, —OCF$_2$CF$_2$CF$_3$), 6.4 (3F, =C—OCH$_2$CF(CF$_3$)—), 5.0 (3F, —OCF$_2$CF$_2$CF$_3$), 4.75–3.86 (4F, —OCF$_2$CF$_2$CF$_3$ and —OCH$_2$CF(CF$_3$)OCF$_2$—) and 3.5 (3F, —CF(CF$_3$)—OCF$_2$CF$_2$CF$_3$).

EXAMPLE 2

Preparation of

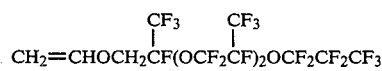
    CF$_3$   CF$_3$
     |       |
CH$_2$=CHOCH$_2$CF(OCF$_2$CF)$_2$OCF$_2$CF$_2$CF$_3$ In the same manner as in Example 1 but using

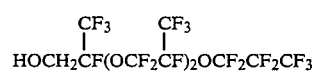
    CF$_3$   CF$_3$
     |       |
HOCH$_2$CF(OCF$_2$CF)$_2$OCF$_2$CF$_2$CF$_3$ (430 g) in place of

    CF$_3$   CF$_3$
     |       |
HOCH$_2$CFOCF$_2$CFOCF$_2$CF$_2$CF$_3$, the reaction was carried out to obtain the title compound (208 g). B.P. 95°–97° C./20 mmHg. Purity 99.5% by weight.

Ir spectrum: 1,620–1,660 cm$^{-1}$ (vinyl group).

$^1$H-NMR (No solvent. Internal standard: TMS): δ(ppm)=6.54

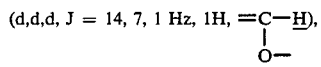
(d,d,d, J = 14, 7, 1 Hz, 1H, =C—H̲),
                                 |
                                 O—

4.45 (d, J=11 Hz, 2H, —OCH̲$_2$CF—), 4.42

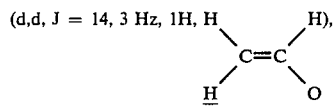
(d,d, J = 14, 3 Hz, 1H, H    H),
                        \\   /
                         C=C
                        /   \\
                       H̲     O and 4.18

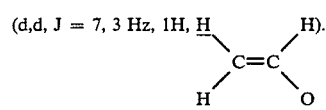
(d,d, J = 7, 3 Hz, 1H, H̲    H).
                       \\   /
                        C=C
                       /   \\
                      H     O $^{19}$F-NMR (No solvent. External standard: trifluoroacetic acid): (ppm)=67.9 (2F, —(OCF$_2$CF (CF$_3$))$_2$—), 56.8 (1F, =C—OCH$_2$CF(CF$_3$)—), 53.0 (2F, —OCF$_2$CF$_2$CF$_3$), 6.4 (3F, =C—OCH$_2$CF(CF$_3$)—), 5.0 (3F, —OCF$_2$CF$_2$CF$_3$), 4.77–3.66 (4F, —OCF$_2$—CF$_2$CF$_3$ and —(OCF$_2$CF(CF$_3$))$_2$) and 3.4 (6F, —(OCF$_2$CF(CF$_3$))$_2$—).

EXAMPLE 3

Homopolymerization of

        CF$_3$   CF$_3$
         |       |
CH$_2$=CHOCH$_2$CFOCF$_2$CFOCF$_2$CF$_2$CF$_3$ To a 100 ml four-necked flask equipped with a stirrer, a nitrogen inlet, an outlet and a thermometer, dichloromethane dehydrated with calcium hydride was added in a nitrogen stream. With cooling the flask at 0° C. with a freezing mixture of ice water and sodium chloride, the fluorooxyalkyl ether, which was produced in Example 1 and dehydraged with calcium hydride, was dropwise added and then BF$_3$—(OC$_2$H$_5$)$_2$ (0.04 ml) was injected with vigorous stirring to initiate polymerization. The reaction was carried out at a room temperature for 24 hours. The reaction mixture was poured in petroleum ether to precipitate the product, which was filtered off with a glass filter and dried at 80° C. under reduced pressure of 30 mmHg to obtain the polymer (15 g). Glass transition temperature, −54.5°−−66.7° C.

T$_g$ of the polymer is measured by a differential scanning calorimeter and defined as the temperature at which heat is absorbed when temperature is raised at a rate of 20° C./min. in a mitrogen stream.

EXAMPLE 4

Copolymerization of

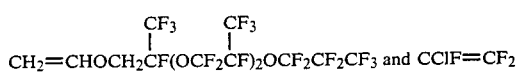

To a 250 ml stainless steelk autoclave, the fluorooxyalkyl vinyl ether produced in Example 2 (25.5 g), 1,1,2-trichloro-1,2,2-trifluoroethane (50 ml) and diisopropyl peroxydicarbonate (0.5 g) were added. After sealing the autoclave, it was cooled with liquid nitrogen to solidify the mixture and evacuated. Then, nitrogen gas was jetted to pressurize to 1 kg/cm²G and the mixture was warmed to a room temperature. The solidification, evacuation and melting procedure was repeated twice. Thereafter, the mixture was solidified with liquid nitrogen, and the autoclave was evacuated. After warming the mixture to room temperature, $CClF=CF_2$ (5.2 g) was added and heated to 40° C. to initiate copolymerization. The reaction was carried out at the same temperature for 71 hours with shaking. The reaction mixture was poured in petroleum ether to precipitate the white product, which was washed with water and dried at 80° C. under reduced for 16 hours to obtain the copolymer (31.3 g). Chlorine content, 5.1% by weight (Calculated, 5.0% by weight). Molar ratio of the fluorooxyalkyl vinyl ether to chlorotrifluoroethylene=47:53. Glass transition temperature, −18.8°−−23.3° C.

COMPARATIVE EXAMPLE 1

Homopolymerization of

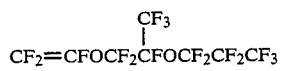

In the same manner as in Example 3 but using the title monomer (40 g), the reaction was carried out. The reaction mixture was poured in petroleum ether to obtain the oily product (5 g) but no polymer.

COMPARATIVE EXAMPLE 1 copolymerization of

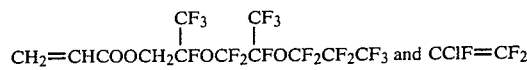

In the same manner as in Example 4 but using the title ether (22 g) in place of the fluorooxyalkyl vinyl ether of the invention, the reaction was carried out. The white powder found in the reaction mixture was filtered, and the filtrate was poured in petroleum ether to precipitate the white solid. The chlorine content in the white powder was 30.5% by weight but no chlorine was found in the white solid. This meant that the title two monomers were not copolymerized.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A polymer comprising a fluorooxyalkyl vinyl ether of the formula:

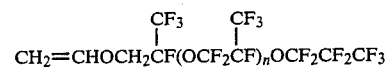

wherein n is an integer of 0 to 5.

2. A polymer according to claim 1, which is a homopolymer.

3. a copolymer comprising a fluorooxyalkyl vinyl ether of the formula:

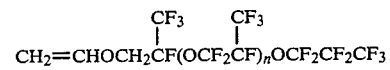

wherein n is an integer of 0 to 5, with a fluoroolefin of the formula:

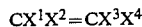

wherein $X^1$, $X^2$, $X^3$, and $X^4$ are the same or different, and are hydrogen, fluorine, chlorine, or trifluoromethyl, provided that at least one of them is fluorine or trifluoromethyl.

4. A copolymer according to claim 3, wherein the fluoroolefin is a member selected from the group consisting of tetrafluoroethylene, chlorotrifluoroethylene and trifluoroethylene.

* * * * *